United States Patent
Peterson, II et al.

(10) Patent No.: US 9,364,572 B2
(45) Date of Patent: Jun. 14, 2016

(54) STATIC FLUID DISINFECTING SYSTEMS AND RELATED METHODS

(71) Applicants: Qore Systems LLC, Tempe, AZ (US); Coating Systems Laboratories, Inc., Chandler, AZ (US)

(72) Inventors: William R. Peterson, II, Chandler, AZ (US); William R. Peterson, III, Gilbert, AZ (US)

(73) Assignees: Coating Systems Laboratories, Inc., Chandler, AZ (US); Qore Systems LLC, Tempe, AZ (US)

( * ) Notice: Subject to any disclaimer, the term of this patent is extended or adjusted under 35 U.S.C. 154(b) by 0 days.

(21) Appl. No.: 14/226,720

(22) Filed: Mar. 26, 2014

(65) Prior Publication Data

US 2014/0212333 A1 Jul. 31, 2014

Related U.S. Application Data

(63) Continuation-in-part of application No. 10/850,121, filed on May 19, 2004, now abandoned.

(60) Provisional application No. 61/805,477, filed on Mar. 26, 2013, provisional application No. 60/472,429, filed on May 22, 2003.

(51) Int. Cl.
| | |
|---|---|
| *A61L 2/00* | (2006.01) |
| *A61L 9/00* | (2006.01) |
| *B01D 11/02* | (2006.01) |
| *A61L 2/235* | (2006.01) |
| *A23L 3/3463* | (2006.01) |

(Continued)

(52) U.S. Cl.
CPC ............... *A61L 2/235* (2013.01); *A23L 3/3463* (2013.01); *A23L 3/358* (2013.01); *C02F 1/50* (2013.01)

(58) Field of Classification Search
CPC .............. A61L 2/00; C02F 1/00; C02F 11/00
USPC .................................. 422/1, 28, 32, 261, 292
See application file for complete search history.

(56) References Cited

U.S. PATENT DOCUMENTS

| | | |
|---|---|---|
| 3,560,385 A | 2/1971 | Roth |
| 3,730,701 A | 5/1973 | Isquith et al. |

(Continued)

FOREIGN PATENT DOCUMENTS

| | | |
|---|---|---|
| CA | 1217004 | 1/1987 |
| EP | 675128 A1 | 10/1995 |

(Continued)

OTHER PUBLICATIONS

Isquith et al., "Surface-Bonded Antimicrobial Activity of an Organosilicon Quaternary Ammonium Chloride", Applied Microbiology, 24(6):859-863(Dec. 1972).*

(Continued)

*Primary Examiner* — Monzer R Chorbaji
(74) *Attorney, Agent, or Firm* — Adam R. Stephenson, LTD.

(57) ABSTRACT

Static fluid disinfecting system and related methods. Implementations of a method of disinfecting a fluid include statically contacting a fluid included in in a container with an open-celled foam where the open-celled foam is coated with a quaternary organosilane coating produced from a quaternary ammonium organosilane reagent where the fluid contains one or more microorganisms.

4 Claims, 6 Drawing Sheets

Figure 1:
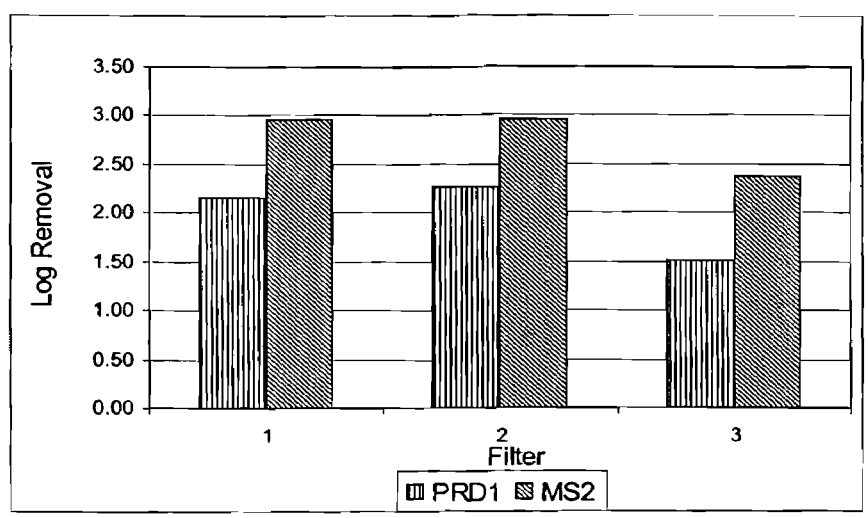

(51) Int. Cl.
  *A23L 3/358*  (2006.01)
  *C02F 1/50*  (2006.01)

(56) References Cited

U.S. PATENT DOCUMENTS

| | | | |
|---|---|---|---|
| 3,794,736 | A | 2/1974 | Abbott et al. |
| 3,817,739 | A | 6/1974 | Abbott et al. |
| 3,860,709 | A | 1/1975 | Abbott et al. |
| 3,865,728 | A | 2/1975 | Abbott et al. |
| 4,005,025 | A | 1/1977 | Kinstedt |
| 4,005,028 | A | 1/1977 | Heckert et al. |
| 4,005,030 | A | 1/1977 | Heckert et al. |
| 4,161,518 | A | 7/1979 | Wen et al. |
| 4,282,366 | A | 8/1981 | Eudy |
| 4,394,378 | A | 7/1983 | Klein |
| 4,395,454 | A | 7/1983 | Baldwin |
| 4,406,892 | A | 9/1983 | Eudy |
| 4,408,996 | A | 10/1983 | Baldwin |
| 4,411,928 | A | 10/1983 | Baldwin |
| 4,414,268 | A | 11/1983 | Baldwin |
| 4,421,796 | A | 12/1983 | Burril et al. |
| 4,425,372 | A | 1/1984 | Baldwin |
| 4,467,013 | A | 8/1984 | Baldwin |
| 4,564,456 | A | 1/1986 | Homan |
| 4,567,039 | A | 1/1986 | Stadnick et al. |
| 4,615,882 | A | 10/1986 | Stockel |
| 4,631,273 | A | 12/1986 | Blehm et al. |
| 4,631,297 | A * | 12/1986 | Battice et al. ............... 521/78 |
| 4,682,992 | A | 7/1987 | Fuchs |
| 4,772,593 | A | 9/1988 | Whalen et al. |
| 4,781,974 | A | 11/1988 | Bouchette et al. |
| 4,797,420 | A | 1/1989 | Bryant |
| 4,847,088 | A | 7/1989 | Blank |
| 4,908,355 | A | 3/1990 | Gettings et al. |
| 5,013,459 | A | 5/1991 | Gettings et al. |
| 5,064,613 | A | 11/1991 | Higgs et al. |
| 5,124,359 | A | 6/1992 | Wachman et al. |
| 5,281,414 | A | 1/1994 | Stockel |
| 5,359,104 | A | 10/1994 | Higgs et al. |
| 5,411,585 | A | 5/1995 | Avery et al. |
| 5,662,808 | A | 9/1997 | Blaney et al. |
| 5,855,788 | A | 1/1999 | Everhart et al. |
| 5,954,869 | A | 9/1999 | Elfersy et al. |
| 6,071,542 | A | 6/2000 | Tanimoto et al. |
| 6,146,688 | A | 11/2000 | Morgan et al. |
| 6,187,192 | B1 | 2/2001 | Johnston et al. |
| 6,402,819 | B1 | 6/2002 | De Ruiter et al. |
| 6,572,926 | B1 | 6/2003 | Morgan et al. |
| 6,613,755 | B2 | 9/2003 | Peterson et al. |
| 2001/0009239 | A1 | 7/2001 | Shiau et al. |
| 2006/0021302 | A1 | 2/2006 | Bernard |
| 2010/0055142 | A1 | 3/2010 | Heagle et al. |

FOREIGN PATENT DOCUMENTS

| | | |
|---|---|---|
| EP | 1493452 B1 | 1/2005 |
| GB | 1433303 | 4/1976 |
| GB | 2160792 | 2/1986 |
| WO | WO 97/42200 | 11/1997 |
| WO | WO 00/72850 | 12/2000 |

OTHER PUBLICATIONS

International Search Report and Written Opinion dated Aug. 7, 2014, PCT/US2014/031922.

Isquith et al., "Surface-bonded antimicrobial activity of an organosilicon quaternary ammonium chloride"; Applied Microbiology, 24(6):859-863 (Dec. 1972).

* cited by examiner

STATIC FLUID DISINFECTING SYSTEMS AND RELATED METHODS

CROSS REFERENCE TO RELATED APPLICATIONS

This document claims the benefit of the filing date of U.S. Provisional Patent Application 61/805,477, entitled "Static Microbial Fluid Disinfection Utilizing Open Cell Substrates Treated With Organosilane Quaternary Ammonium Chloride Compounds" to William R. Peterson II, et al. which was filed on Mar. 26, 2013, the disclosure of which is hereby incorporated entirely herein by reference.

This application is a continuation-in-part application of the earlier U.S. Utility Patent Application to William R. Peterson II et al., entitled "Antimicrobial Quaternary Ammonium Organosilane Coatings," application Ser. No. 10/850,121, filed May 19, 2004, now pending, which claimed the benefit of the filing date of U.S. Provisional Patent Application 60/472,429 entitled "Water & Fluids Purification With Bonded Quaternary Ammonium Organosilanes," to William R. Peterson II, which was filed on May 22, 2003, the disclosures of which are hereby incorporated entirely herein by reference.

BACKGROUND

1. Technical Field

Aspects of this document relate generally to methods and compositions for reducing the number of microorganisms in a liquid using a solid phase carrier coated with a quaternary ammonium organosilane coating.

2. Background Art

Quaternary ammonium organosilanes have been used in a wide variety of applications. U.S. Pat. No. 6,613,755 to Peterson II et al. entitled "Antimicrobial Skin Preparations Containing Organosilane Quaternaries," issued Sep. 2, 2003, discloses various examples of uses of quaternary ammonium organosilane compounds that have antimicrobial properties.

SUMMARY

Implementations of systems for disinfecting fluids may include: an open-celled foam that includes a range of pores per inch (PPI) between 10 PPI and 110 PPI where the open-celled foam is coated with a quaternary organosilane coating produced from a quaternary ammonium organosilane coating produced from a quaternary ammonium organosilane reagent having the formula:

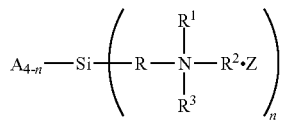

A may be a member independently selected from the group consisting of —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein $R^4$ may be a member selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R may be substituted or unsubstituted alkylene; $R^1$, $R^2$, and $R^3$ may be members each independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl; and substituted or unsubstituted heteroaryl; Z may be a member selected from the group consisting of fluoride, chloride, bromide, iodide, tosylate, hydroxide, sulfate, and phosphate; and n may be 1, 2, or 3. A container may be included that encloses the open-celled foam and places the open-celled foam in static contact with a fluid included in the container where the fluid includes one or more microorganisms selected from the group consisting of *Cryptosporidium parvum* and *Giardia*.

Implementations of systems for disinfecting fluids may include one, all, or any of the following:

The open-celled foam may include a material selected from the group consisting of naturally occurring and synthetic organic polymeric materials, stainless steel, copper, silicon, carbon, and silicon carbide.

The one or more microorganisms are also selected from the group consisting of encapsulated and non-encapsulated viruses, Gram-negative and Gram positive bacteria, fungi, mold, spores, yeast, and protozoic bacteria.

The fluid may be turbid.

The fluid may be optically opaque.

The fluid may include a hydrocarbon and water emulsion.

The container may further include a solid material including one or more microorganisms and the open-celled foam may contact one or more surfaces of the solid material.

Implementations of a system for disinfecting a fluid may include an open-celled foam having a surface area per gram less than a surface area per gram of one of filter sand and zeolite where the open-celled foam is coated with a quaternary organosilane coating produced from a quaternary ammonium organosilane reagent having the formula:

A may be a member independently selected from the group consisting of —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^4$ may be a member selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R may be substituted or unsubstituted alkylene; $R^1$, $R^2$, and $R^3$ may be members each independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl; and substituted or unsubstituted heteroaryl; Z may be a member selected from the group consisting of fluoride, chloride, bromide, iodide, tosylate, hydroxide, sulfate, and phosphate; and n may be 1, 2, or 3. A container may be included that encloses the open-celled foam and places the open-celled foam in static contact with a fluid comprised in the container where the fluid comprising one or more microorganisms.

Implementations of the system may include one, all, or any of the following:

The microorganisms may be selected from the group consisting of *Cryptosporidium parvum, Giardia*, encapsulated viruses, and non-encapsulated viruses.

The open-celled foam may include a range of pores per inch (PPI) between 10 PPI and 110 PPI.

The open-celled foam comprises a material selected from the group consisting of natural and synthetic organic polymeric materials, stainless steel, copper, silicon, carbon, and silicon carbide.

The fluid may be turbid.

The fluid may be optically opaque.

The fluid may include a hydrocarbon and water emulsion.

The container may include a solid material including one or more microorganisms and the open-celled foam may contact one or more surfaces of the solid material.

Implementations of systems for disinfecting a fluid may utilize implementations of a method of disinfecting a fluid. The method may include statically contacting a fluid included in in a container with an open-celled foam where the open-celled foam is coated with a quaternary organosilane coating produced from a quaternary ammonium organosilane reagent having the formula:

A may be a member independently selected from the group consisting of —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^4$ may be a member selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R may be substituted or unsubstituted alkylene; $R^1$, $R^2$, and $R^3$ may be members each independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl; and substituted or unsubstituted heteroaryl; Z may be a member selected from the group consisting of fluoride, chloride, bromide, iodide, tosylate, hydroxide, sulfate, and phosphate; and n may be 1, 2, or 3. The fluid may include one or more microorganisms.

Implementations of a method of disinfecting a fluid may include one, all, or any of the following:

Statically contacting the fluid included in the container with the open-celled foam may further include where the open-celled foam comprises a range of pores per inch (PPI) between 10 PPI and 110 PPI.

Statically contacting the fluid comprised in the container may further include where the one or more microorganisms in the fluid are selected from the group consisting of *Cryptosporidium parvum, Giardia*, encapsulated viruses, and non-encapsulated viruses.

The method may further include statically contacting one or more surfaces of a solid material including one or more microorganisms included in the container with the open-celled foam.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and:

FIG. 1 illustrates the reduction in the viable number of bacteriophages by quaternary ammonium organosilane coated zeolite;

FIG. 2 illustrates the reduction in the viable number of (A) *K. terriena* bacteria and (B) *E. Coli* bacteria by quaternary ammonium organosilane coated zeolite;

FIG. 3 illustrates the average reduction in the viable number of bacteria and bacteriophages by quaternary ammonium organosilane coated zeolite;

FIG. 4 illustrates the reduction in the viable number of algae by quaternary ammonium organosilane coated zeolite;

FIG. 5 illustrates the reduction in the viable number of protozoa parasites by quaternary ammonium organosilane coated zeolite;

FIG. 6 illustrates an experimental apparatus containing a column packed with quaternary ammonium organosilane coated zeolite for use in decreasing the viable number of microorganisms in a liquid.

DESCRIPTION

This disclosure, its aspects and implementations, are not limited to the specific components, assembly procedures or method elements disclosed herein. Many additional components, assembly procedures and/or method elements known in the art consistent with the intended static fluid disinfecting systems and related method implementations will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such static fluid disinfecting systems, and implementing components and methods, consistent with the intended operation and methods.

Definitions

As used herein, the term "reducing the viable number of microorganisms," means reducing the number of microorganisms capable of growing, working, functioning, and/or developing adequately. The term includes, for example, reducing the overall number of microorganisms, reducing the number of active microorganisms (i.e. inactivating microorganisms), reducing the number of microorganisms able to reproduce, reducing the number of intact microorganisms, reducing the number of infectious agents, removal of microorganisms, inactivation of microorganisms; and/or and the like. "Eliminating the viable number of microorganisms" means reducing the viable number of microorganisms to zero.

The term "microorganism," as used herein, means an organism that, individually, can only be seen through a microscope. The term microorganism includes, for example, bacteria, fungi, actinomycetes, algae, protozoa, yeast, germs, ground pearls, nematodes, viruses, prions, and algae.

The abbreviations used herein have their conventional meaning within the chemical and biological arts.

Where chemical groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched carbon chain containing at least one carbon, which may be fully saturated, mono-or polyunsaturated. An unsaturated alkyl group is one having one or more double bonds or triple bonds. An "unsubstituted alkyl" refers to branched or unbranched alkyl groups wherein the backbone carbons are attached to hydrogen and/or other backbone carbon. The term "alkylene" refers to a divalent radical derivative of an alkyl.

A "backbone carbon" or "backbone heteroatom," as used herein, refers to a carbon or heteroatom, respectively, that is not at the point of attachment of an alkyl or heteroalkyl group, and which forms part of a branched or unbranched chain containing at least one carbon.

The term "alkoxy," refers to those alkyl groups attached to the remainder of the molecule via an oxygen atom.

The term "alkylether" refers to an alkyl having at least one carbon-oxygen-carbon linkage.

The term "hydroxy-substituted alkyl" refers to an alkyl having at least one attached hydroxyl group.

The term "amine-substituted alkyl" refers to an alkyl having at least one attached primary, secondary, or tertiary amine group.

The term "hetero alkyl," by itself or in combination with another term, means an alkyl having at least one heteroatom within the carbon chain. The heteroatom is selected from the group consisting of O, N, and S, wherein the nitrogen and sulfur atoms may optionally be oxidized and the nitrogen heteroatom may optionally be quaternized. The heteroatom(s) O, N, and S may be placed at any interior position of the heteroalkyl group or at the position at which the alkyl group is attached to the remainder of the molecule. Up to two heteroatoms may be consecutive, such as, for example, —$CH_2$—NH—$OCH_3$. Similarly, the term "heteroalkylene" by itself or as part of another substituent means a divalent radical derived from heteroalkyl. For heteroalkylene groups, heteroatoms can also occupy either or both of the chain termini.

An "unsubstituted heteroalkyl" refers to branched or unbranched heteroalkyl groups wherein the backbone carbons are attached to hydrogen, other backbone carbons, and/or backbone heteroatoms. The backbone heteroatoms are attached to hydrogen, backbone carbons, other backbone heteroatoms, and/or oxygen (in the case of oxidized sulfur).

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. The terms "cycloalkylene" and "heterocycloalkylene" refer to the divalent derivatives of cycloalkyl and heterocycloalkyl groups, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl.

The term "aryl" means, unless otherwise stated, a polyunsaturated, aromatic, hydrocarbon which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the heteroatom occupies a ring vertex (also referred to herein as a "ring heteroatom"). The nitrogen and sulfur atoms are optionally oxidized, and the nitrogen atom(s) are optionally quaternized. A heteroaryl group can be attached to the remainder of the molecule through a carbon or heteroatom. The terms "arylene" and "heteroarylene" refer to the divalent derivatives of aryl and heteroaryl groups, respectively.

An "unsubstituted aryl" or "unsubstituted heteroaryl" refers to aryl and heteroaryl rings, respectively, in which the carbon atoms occupying ring vertices that are not at a point of attachment to the remainder of the molecule are attached only to hydrogen or other atoms occupying ring vertices. Heteroatoms occupying ring vertices that are not at a point of attachment to the remainder of the molecule are attached only to hydrogen, other atoms occupying ring vertices, or oxygen (in the case of oxidized ring heteroatoms).

The term "oxo" as used herein means an oxygen that is double bonded to a carbon atom.

A "liquid," as used herein, is a substance that flows freely, lacks crystal structure, and, unlike a gas, retains the same volume independent of the shape of its container at ambient temperature and pressure. An "aqueous liquid" refers to a liquid having a portion of water. Aqueous liquids suitable for the practice of the present invention include, for example, waste water and sewage water, fruit juices, milk, and medical fluids. Other suitable fluids will be readily determined by those skilled in the art and may be utilized in various implementations.

A "solid," as used herein, is a substance that does not dissolve in water at ambient temperature. Thus, a "solid phase carrier" is a carrier that is insoluble in water at ambient temperature.

Methods

In one aspect, the present invention provides a method of reducing or eliminating the viable number of microorganisms in a liquid. The method includes contacting the liquid with a solid phase carrier coated with a quaternary ammonium organosilane coating. The quaternary ammonium organosilane coating may reduce the viable number of microorganisms in a liquid by directly contacting the microorganisms.

A wide variety of solid phase carriers are useful in conjunction with the methods and compositions of the present invention. The solid phase carrier may be any appropriate dimension or shape, including, for example, a planar surface, the lining of tubing or pipe, or a roughly spherical particle. The solid phase carrier may also be any appropriate size, including, for example, a microscopic carrier, a carrier detectable with the naked eye, a roughly planar carrier with dimensions that are centimeters to meters in length, and roughly spherical carrier with a radius that is centimeters to meters in length.

The solid phase carrier is typically composed of one or more substance or material that is insoluble in liquid media (e.g. organic media, aqueous media, water, etc.). Exemplary materials include glass, silica, sand (e.g. manganese greensand and filter sand), quartz, flint, zeolite, anthracite, activated carbon, garnet, ilmenite, benn, aluminum (including non-hydrous aluminum silicate (e.g. filter AG), oxides of iron and titanium (e.g. ilmenite), diatomaceous earth, pozzolan (silicon/alumina material that occurs naturally and is produced as a byproduct of coal combustion), metal (e.g. tin), ceramic, and/or organic polymers and plastics (e.g. high density polyethylene (HDPE), polypropylene (PP) or polyvinyl chloride (PVC)).

In various implementations, the liquid is contacted with an additional solid phase carrier. The additional solid phase carrier may be coated with a different quaternary ammonium organosilane coating than the solid phase carrier. The additional solid phase carrier may also be composed of a different material than the solid phase carrier.

Quaternary Ammonium Organosilane Reagents

The solid phase carriers of the current invention are coated with a quaternary ammonium organosilane coating. The quaternary ammonium organosilane coating is produced from a quaternary ammonium organosilane reagent. The quaternary ammonium organosilane reagent has the formula:

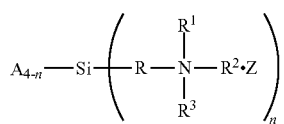

Formula I

In Formula (I), A is selected from —OR$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Where more than one A is present, each A is independently selected from the groups recited above or below.

R$^4$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

R is selected from substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene.

R$^1$, R$^2$, and R$^3$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Z is selected from fluoride, chloride, bromide, iodide, tosylate, hydroxide, sulfate and phosphate.

The symbol n is 1, 2 or 3.

In an exemplary implementation, each substituted alkyl, substituted heteroalkyl, substituted cycloalkyl, substituted heterocycloalkyl, substituted aryl, and substituted heteroaryl described herein as possible A, R$^1$, R$^2$, R$^3$, and R$^4$ moieties are substituted only with at least one substituent independently selected from —OH, unsubstituted (C$_1$-C$_5$)alkyl, unsubstituted 2 to 5 membered heteroalkyl, unsubstituted (C$_5$-C$_7$) membered cycloalkyl, unsubstituted 5 to 7 membered heterocycloalkyl, unsubstituted aryl, and unsubstituted heteroaryl. For example, where A is a substituted (C$_1$-C$_{10}$)alkyl, the substituted (C$_1$-C$_{10}$)alkyl is substituted only with at least one substituent independently selected from —OH, unsubstituted (C$_1$-C$_5$)alkyl, unsubstituted 2 to 5 membered heteroalkyl, unsubstituted (C$_5$-C$_7$) membered cycloalkyl, unsubstituted 5 to 7 membered heterocycloalkyl, unsubstituted aryl, and unsubstituted heteroaryl.

In other implementations, each substituted alkyl, substituted heteroalkyl, substituted cycloalkyl, substituted heterocycloalkyl, substituted aryl, and substituted heteroaryl described herein as possible A, R$^1$, R$^2$, R$^3$, and R$^4$ moieties are substituted only with at least one substituent independently selected from —OH, unsubstituted (C$_1$-C$_5$)alkyl, unsubstituted 2 to 5 membered heteroalkyl, unsubstituted (C$_5$-C$_7$) membered cycloalkyl, unsubstituted 5 to 7 membered heterocycloalkyl, unsubstituted aryl, and unsubstituted heteroaryl. In other implementations, each substituted alkyl, substituted heteroalkyl, substituted cycloalkyl, substituted heterocycloalkyl, substituted aryl, and substituted heteroaryl described herein as possible A, R$^1$, R$^2$, R$^3$, and R$^4$ moieties are substituted only with at least one substituent independently selected from —OH, unsubstituted (C$_1$-C$_5$)alkyl, unsubstituted (C$_5$-C$_7$) membered cycloalkyl, and unsubstituted phenyl. In yet other implementations, each substituted alkyl, substituted heteroalkyl, substituted cycloalkyl, substituted heterocycloalkyl, substituted aryl, and substituted heteroaryl described herein as possible A, R$^1$, R$^2$, R$^3$, and R$^4$ moieties are substituted only with at least one unsubstituted (C$_1$-C$_3$)alkyl.

In another exemplary embodiment, each substituted alkylene, substituted heteroalkylene, substituted cycloalkylene, substituted heterocycloalkylene, substituted arylene, and substituted heteroarylene described herein as possible R moieties are substituted only with at least one substituent independently selected from —OH, unsubstituted (C$_1$-C$_5$)alkyl, unsubstituted 2 to 5 membered heteroalkyl, unsubstituted (C$_5$-C$_7$) membered cycloalkyl, substituted 5 to 7 membered heterocycloalkyl, unsubstituted aryl, and unsubstituted heteroaryl.

In various implementations, each substituted alkylene, substituted heteroalkylene, substituted cycloalkylene, substituted heterocycloalkylene, substituted arylene, and substituted heteroarylene described herein as possible R moieties are substituted only with at least one substituent independently selected from —OH, unsubstituted (C$_1$-C$_5$)alkyl, unsubstituted 2 to 5 membered heteroalkyl, unsubstituted (C$_5$-C$_7$) membered cycloalkyl, unsubstituted 5 to 7 membered heterocycloalkyl, unsubstituted aryl, and unsubstituted heteroaryl. In other implementations, each substituted alkylene, substituted heteroalkylene, substituted cycloalkylene, substituted heterocycloalkylene, substituted arylene, and substituted heteroarylene described herein as possible R moieties are substituted only with at least one substituent independently selected from —OH, unsubstituted (C$_1$-C$_5$)alkyl, unsubstituted (C$_5$-C$_7$) membered cycloalkyl, and unsubstituted phenyl. In yet other implementations, each substituted alkylene, substituted heteroalkylene, substituted cycloalkylene, substituted heterocycloalkylene, substituted arylene, and substituted heteroarylene described herein as possible R moieties are substituted only with at least one unsubstituted (C$_1$-C$_3$)alkyl.

A may be selected from —OR$^4$, substituted or unsubstituted (C$_1$-C$_{10}$)alkyl, substituted or unsubstituted 2 to 12 membered heteroalkyl, substituted or unsubstituted (C$_5$-C$_7$) cycloalkyl, substituted or unsubstituted 5 to 7 membered heterocycloalkyl, substituted or unsubstituted aryl, and substituted or unsubstituted heteroaryl. R$^4$ may be selected from hydrogen, substituted or unsubstituted (C$_1$-C$_{10}$)alkyl, substituted or unsubstituted 2 to 10 membered heteroalkyl, substituted or unsubstituted (C$_5$-C$_7$)cycloalkyl, substituted or unsubstituted 5 to 7 membered heterocycloalkyl, substituted or unsubstituted aryl, and substituted or unsubstituted heteroaryl.

In some implementations, A is selected from —OR$^4$, unsubstituted (C$_1$-C$_{10}$)alkyl, unsubstituted 2 to 12 membered heteroalkyl, unsubstituted ($C_5$-$C_7$)cycloalkyl, unsubstituted 5 to 7 membered heterocycloalkyl, unsubstituted aryl, and unsubstituted heteroaryl. In other implementations, A is selected from —$OR^4$, unsubstituted ($C_1$-$C_{10}$)alkyl, unsubstituted 3 to 12 membered alkylether, unsubstituted ($C_5$-$C_7$) cycloalkyl, and unsubstituted phenyl.

A may be selected from —$OR^4$, unsubstituted ($C^1$-$C^4$) alkyl, unsubstituted 3 to 8 membered alkylether, unsubstituted ($C^5$-$C^7$)cycloalkyl, and unsubstituted phenyl. Alternatively, A is selected from —$OR^4$, unsubstituted ($C_1$-$C_4$)alkyl, and unsubstituted 3 to 8 membered alkylether.

$R^4$ may be selected from hydrogen, unsubstituted ($C_1$-$C_{10}$) alkyl, unsubstituted 2 to 12 membered heteroalkyl, unsubstituted ($C_5$-$C_7$)cycloalkyl, unsubstituted 5 to 7 membered heterocycloalkyl, unsubstituted aryl, and unsubstituted heteroaryl.

In some implementations, $R^4$ is selected from hydrogen, unsubstituted ($C_1$-$C_{10}$)alkyl, unsubstituted 3 to 12 membered alkylether, unsubstituted ($C_5$-$C_7$)cycloalkyl, and unsubstituted phenyl. In a related embodiment, $R^4$ is selected from hydrogen, unsubstituted ($C_1$-$C_8$)alkyl, unsubstituted 3 to 8 membered alkyl ether, unsubstituted ($C_5$-$C_7$)cycloalkyl, and unsubstituted phenyl. Alternatively, $R^4$ is selected from hydrogen, unsubstituted ($C_1$-$C_8$)alkyl, and unsubstituted 3 to 8 membered alkyl ether.

$R^4$ may also be selected from phenyl, methylphenyl, substituted or unsubstituted ($C_1$-$C_8$)alkyl, and —$(CH_2)_x$—O—$(CH_2)_y CH_3$. X and y are integers independently selected from 1 to 10.

R may be selected from substituted or unsubstituted ($C_1$-$C_{10}$) alkylene, substituted or unsubstituted 2 to 10 membered heteroalkylene, substituted or unsubstituted ($C_5$-$C_7$)cycloalkylene, substituted or unsubstituted 2 to 7 membered heterocycloalkylene, substituted or unsubstituted arylene, and substituted or unsubstituted heteroarylene.

In various implementations, R is a member selected from unsubstituted ($C_1$-$C_{10}$)alkylene, unsubstituted 2 to 10 membered heteroalkylene, unsubstituted ($C_5$-$C_7$)cycloalkylene, unsubstituted 5 to 7 membered heterocycloalkylene, unsubstituted arylene, and unsubstituted heteroarylene.

R may also be unsubstituted ($C_1$-$C_{10}$)alkylene.

$R^1$, $R^2$, and $R^3$ may be selected from hydrogen, substituted or unsubstituted ($C_1$-$C_{20}$)alkyl, substituted or unsubstituted 2 to 20 membered heteroalkyl, substituted or unsubstituted ($C_5$-$C_7$)cycloalkyl, substituted or unsubstituted 5 to 7 membered heterocycloalkyl, substituted or unsubstituted aryl, and substituted or unsubstituted heteroaryl.

In some implementations, $R^1$, $R^2$, and $R^3$ are independently selected from hydrogen, unsubstituted ($C_1$-$C_{20}$)alkyl, hydroxy-substituted ($C_1$-$C_{20}$)alkyl, amine-substituted ($C_1$-$C_{20}$)alkyl, unsubstituted 2 to 20 membered heteroalkyl, unsubstituted ($C_5$-$C_7$)cycloalkyl, unsubstituted 5 to 7 membered heterocycloalkyl, unsubstituted aryl, and unsubstituted heteroaryl. In a related embodiment, $R^1$, $R^2$, and $R^3$ are independently selected from hydrogen, unsubstituted ($C_1$-$C_{20}$) alkyl, unsubstituted alkylether, hydroxy-substituted ($C_1$-$C_{20}$) alkyl, amine-substituted ($C_1$-$C_{20}$)alkyl, unsubstituted ($C_5$-$C_7$)cycloalkyl, and unsubstituted phenyl.

$R^1$, $R^2$, and $R^3$ may also be selected from hydrogen, unsubstituted ($C_1$-$C_{20}$)alkyl, unsubstituted alkylether, hydroxy-substituted ($C_1$-$C_{20}$)alkyl, amine-substituted ($C_1$-$C_{20}$)alkyl, unsubstituted ($C_5$-$C_7$)cycloalkyl, and unsubstituted phenyl. Alternatively, $R^1$, $R^2$, and $R^3$ are selected from hydrogen, unsubstituted ($C_1$-$C_{20}$)alkyl, unsubstituted alkylether, hydroxy-substituted ($C_1$-$C_{20}$)alkyl, and amine-substituted ($C_1$-$C_{20}$)alkyl.

In other exemplary embodiments, $R^1$, $R^2$, and $R^3$ are independently selected from —$(CH_2)_q OCH_3$, —$(CH_2)_q OH$, —$(CH_2)_q O(CH_2)_t CH_3$, —$(CH_2)_q NHCH_3$, —$(CH_2)_q NH_2$, —$(CH_2)_q N(CH_3)_2$ and —$(CH_2)_q NH_2(CH_2)_t CH_3$, in which q and t are integers independently selected from 0 to 10. $R^1$, $R^2$, and $R^3$ may also be independently selected from the group consisting of —$CH_2CH_2OCH_3$ and —$CH_2CH_2OCH_2CH_2CH_3$. Alternatively, $R^1$, $R^2$, and $R^3$ may also be independently selected from —$CH_2CH_2OH$ and —$CH_2CH_2CH_2CH(OH)CH_3$. $R^1$, $R^2$, and $R^3$ may also be independently selected from —$CH_2CH_2NH_2$ and —$CH_2CH_2N(CH_3)_2$. Finally, $R^1$, $R^2$, and $R^3$ may be members independently selected from methyl, octadecyl, didecyl, and tetradecyl.

In an exemplary embodiment, the quaternary ammonium organosilane reagent is selected from $(CH_3O)_3Si(CH_2)_3N^+$ $(CH_3)_2(C_{18}H_{37})$ $(Cl^-)$; $(CH_3CH_2O)_3Si(CH_2)_3N^+(CH_3)_2$ $(C_{18}H_{37})$ $(Cl^-)$; $(CH_3O)_3Si(CH_2)_3N^+(CH_3)_2(C_{18}H_{37})$ $(Br^-)$; $(CH_3O)_3Si(CH_2)_3N^+(C_{10}H_{21})_2(CH_3)$ $(Cl^-)$; $(CH_3O)_3Si$ $(CH_2)_3N^+(CH_3)_2(C_{14}H_{29})$ $(Cl^-)$; $(CH_3O)_3Si(CH_2)_3N^+$ $(CH_3)_2$ $(C_{14}H_{29})$ $(Br^-)$; and $(CH_3O)_3Si(CH_2)_3N^+(CH_3)_2$ $(C_{16}H_{33})$ $(Cl^-)$. In a related embodiment, the quaternary ammonium organosilane reagent is selected from 3-(trimethoxysilyl)propyldimethyloctadecyl ammonium chloride, 3-(trimethoxysilyl)propyldidecylmethyl ammonium chloride, and 3-(trimethoxysilyl)propyldimethyltetradecyl ammonium chloride.

In another exemplary embodiment, the quaternary ammonium organosilane contains an ammonium halide and a hydrolyzable alkoxy group bonded to silicon.

Quaternary Ammonium Organosilane Coatings

A variety of methods may be used to form the quaternary ammonium organosilane coatings from quaternary ammonium organosilane reagents. The quaternary ammonium organosilane reagent may be applied to the solid phase carrier using any method known in the art, including, for example, methods for covalently or non-covalently binding the quaternary ammonium organosilane reagent to the solid phase carrier to form a quaternary ammonium organosilane coating.

Solid phase carriers may be contacted (e.g. sprayed, dipped, or otherwise applied) with a solution preparation containing the quaternary ammonium organosilane reagent. In some embodiments, the quaternary ammonium organosilane reagent coated surfaces are allowed to air dry at room temperatures for a sufficient period of time to complete a condensation cure of the quaternary ammonium organosilane coating. Alternatively, heat is applied to the coated surfaces for a sufficient period of time to effect cure, the duration and temperature of such is known to those skilled in the art.

In various implementations, the quaternary ammonium organosilane reagent is covalently bound to the solid phase carrier. Typically, the quaternary ammonium organosilane reagent is covalently bound to an accessible carrier reactive group that forms a part of the solid phase carrier. A variety of reactive groups are useful in covalently binding the quaternary ammonium organosilane reagent. The quaternary ammonium organosilane reagent may be covalently bound to the carrier reactive group through the silane moiety of the quaternary ammonium organosilane reagent. The silane moiety, as used herein, refers to the $A_{4-n}$-S— portion of the compound Formula I.

The silane moiety may be covalently bound to the carrier reactive group by allowing the carrier reactive group to covalently bind to the silicon atom of the silane moiety. For example, where the carrier reactive group is a hydroxyl, the oxygen atom may be allowed to bind to the silicon atom to form a silicon-oxygen bond thereby covalently attaching the quaternary ammonium organosilane reagent to the carrier molecule. In a related embodiment, the silane moiety includes at least one —OR$^4$ that leaves upon attack of a hydroxyl carrier reactive group. This reaction may be referred to herein as a condensation reaction. Thus, the quaternary ammonium organosilane reagent may be covalently attached to the carrier molecule via a condensation reaction.

The silane moiety may also include an A group that contains a reactive group, referred to herein as a silane reactive group. The silane reactive group is capable of reacting with a carrier reactive group to form a covalent bond.

Silane reactive groups, carrier reactive groups and classes of reactions useful in covalently attaching quaternary ammonium organosilane reagents to a solid phase carrier are generally those that are well known in the art of bioconjugate chemistry. These include, but are not limited to nucleophilic substitutions (e.g. reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, *Advanced Organic Chemistry*, 3rd Ed., John Wiley & Sons, New York, 1985; Hermanson, *Bioconjugate Techniques*, Academic Press, San Diego, 1996; and Feeney et al., *Modification Of Proteins;* Advances in Chemistry Series, Vol. 198, American Chemical Society, Washington, D.C., 1982 the disclosures of which are hereby incorporated herein entirely by reference.

Useful silane and carrier reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the quaternary ammonium organosilane coating. Alternatively, a silane or carrier reactive functional group can be protected from participating in the reaction by the presence of a protecting group. Those of skill in the art will understand how to protect a particular functional group from interfering with a chosen set of reaction conditions. For examples of useful protecting groups, See Greene et al., *Protective Groups In Organic Synthesis*, John Wiley & Sons, New York, 1991, the disclosure of which is incorporated entirely herein by reference.

Linkers may also be employed to attach the quaternary ammonium organosilane reagent to the solid phase carrier. Linkers may include reactive groups at the point of attachment to the quaternary ammonium organosilane reagent and/or the solid phase carrier. Any appropriate linker may be used in the present invention, including substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene. In an exemplary embodiment, the linker group is selected from substituted or unsubstituted alkylene, and substituted or unsubstituted heteroalkylene. In a related embodiment, the linker is selected from unsubstituted alkylene, alkylene substituted with at least one oxy, unsubstituted heteroalkylene, and heteroalkylene substituted with at least one oxy. In another related embodiment, the linker is selected from unsubstituted ($C_1$-$C_{25}$) alkylene, ($C_1$-$C_{25}$) alkylene substituted with at least one oxy, unsubstituted 2 to 26 membered heteroalkylene, and 2 to 26 membered heteroalkylene substituted with at least one oxy.

Other useful linkers include those having a polyester backbone (e.g. polyethylene glycol), and derivatives thereof. A wide variety of useful linkers are commercially available (e.g. polyethylene glycol based linkers such as those available from Nektar, Inc. of Huntsville, Ala.).

The quaternary ammonium organosilane reagent may also be non-covalently attached to the solid phase carrier using any interaction, such as Van der Waals interactions, hydrophobic interactions, dipole-dipole interactions, electrostatic interactions, and/or hydrogen bonding interactions.

In an exemplary embodiment, the quaternary ammonium organosilane reagent forms a polymeric network that partially or wholly covers the solid phase carrier. Where the quaternary ammonium organosilane reagent forms a polymeric network, the quaternary ammonium organosilane reagent may additionally from a covalent and/or non-covalent bond with the solid phase carrier.

The quaternary ammonium organosilane reagent typically forms a polymeric network by covalently binding through the silane moiety. Where the silane moiety includes at least one —OR$^4$ group, the quaternary ammonium organosilane reagent may form a silicone polymer having a series of silicon-oxygen-silicon bonds. The silicones may be linear polymers or cross-linked polymers. For example, where the silane moiety includes at least two —OR$^4$ groups, the quaternary ammonium organosilane reagent may form a cross-linked silicone polymer wherein each silica atom forms part of at least two silicon-oxygen-silicon bonds. Thus, polymerization may be achieved using silane reactive groups capable of forming intermolecular covalent bonds with other silane reactive groups.

In an exemplary embodiment, the quaternary ammonium organosilane reagent is contacted with an aqueous liquid prior to application to the solid phase carrier. As discussed above, useful quaternary ammonium organosilane reagents include those containing hydrolyzable alkoxy groups bound to the silicon atom. Upon contact with a water molecule, the alkoxy groups (e.g. methoxy) may hydrolyze to form hydroxy substituted silicon atoms (also referred to herein as "silanols")

with simultaneous liberation of alcohol as a by-product of the hydrolysis (also referred to herein as condensation). The resultant compound formed on addition of quaternary ammonium organosilanes of the above compositions are the corresponding mono-, di-, or tri-silanol species. The reactive silanol species prepared upon hydrolysis may form covalent silicon-oxygen-silicon bonds with other silanol species resulting in polymeric coatings as described above. The resultant polymeric coating may be a molecular network non-covalently and/or covalently bonded to the solid phase carrier.

It will be understood by those skilled in the art that the quaternary ammonium organosilane coating may form three dimensional, cross-linked, water-insoluble, polymeric coatings which may contain some uncondensed silanol or alkoxy moieties. Monomeric, dimeric and oligomeric species may be present on the solid phase carrier following application of an aqueous solution containing quaternary ammonium organosilane reagent, and these may bond to the solid phase carrier, whether by covalent or non-covalent mechanisms.

The quaternary ammonium organosilane coatings formed on the solid phase carriers retain their antimicrobial activity. They are substantive to the solid phase carriers and largely insoluble in aqueous liquid. For example, in some embodiments, less than 10 ppb of quaternary ammonium organosilane reagents is detectable in water after Standard 42 testing as performed by NSF International, Ann Arbor, Mich.

In an exemplary embodiment, the quaternary ammonium organosilane coating has the formula:

Formula II

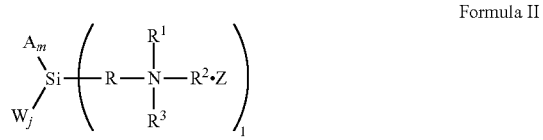

In Formula II, A, R, $R^1$, $R^2$, and $R^3$ are as defined above in Formula I. W is a solid phase carrier as described above. The solid phase carrier W may include a linker moiety and/or the remnant of a reactive group. The symbol 1 represents an integer selected from 1, 2, or 3. The symbols m and j represent integers independently selected from 0, 1, 2, and 3, wherein both m and j are not simultaneously 0. The sum of m, j, and l is not greater than four. In a related embodiment, l is 1, 2, or 3; m is 1, 2, or 3, and j is 1, 2, or 3. In another related embodiment, l is 1; m is 1, 2, or 3, and j is 1, 2, or 3.

Microorganisms

The term "microorganism," as used herein, means an organism that, individually, can only be seen through a microscope. The term microorganism includes, for example, bacteria, fungi, actinomycetes, algae, protozoa, yeast, germs, ground pearls, nematodes, viruses, prions, and algae. Thus, in an exemplary embodiment, the microorganism is selected from bacteria, viruses (also referred to herein as bacteriophages), fungi, algae, mold, yeast, spores, and protozoa parasites. The term "bacteria" includes both gram positive and gram negative bacteria.

Gram positive bacteria include, for example, *Bacillus* sp. (vegetative cell), *Corynebacterium diptheriae*, *Micrococcus lutea*, *Micrococcus* sp., *Mycobacterium tuberculosis*, *Mycobacterium smegmatis*, *Propionibacterium acnes*, *Staphylococcus aureus*, *Staphylococcus epidermidis*, *Streptococcus faecalis*, *Streptococcus mutans*, *Streptococcus pneumonia*, and *Streptococcus pyogenes*.

Gram negative bacteria include, for example, *Acinetobacter calcoaceticus*, *Aeromonas hydrophilia*, *Citrobacter deversus*, *Citrobacter freundi*, *Enterobacter aerogenes*, *Enterobacter aglomera*, *Escherichia coli*, *Klebsiella oxytoca*, *Klebsiella pneumoniae*, *Klebsiella terriena*, *Legionella pneumophila*, *Morganella morganii*, *Proteus mirabilis*, *Proteus vulgaris*, *Pseudomonas aeruginosa*, *Pseudomonas fluorscens*, *Salmonella cholera suis*, *Salmonella typhi*, *Salmonella typhimurium*, *Serratia liquifaciens*, and *Xanthomonas campestris*.

Viruses include, for example, Adenovirus Type II & IV, Bovine Adenovirus Type I & IV, Feline pneumonitis, Herpes Simplex Type I, Herpes Simplex Type II, HIV-1 (AIDS), Influenza A2 (Aichi), Influenza A2 (Asian), Influenza B, Mumps, Parinfluenza (Sendai), Reovirus Type I, Simian Virus 40, Vaccinia, MS2, T2 (non-enveloped virus) and PRD1.

Fungi, algae, mold, yeast, and spores include, for example, *Alterania alternate*, *Aspergillus flavus*, *Aspergillus niger*, *Aspergillus sydowi*, *Aspergillus terreus*, *Aspergillus versicolor*, *Aspergillus verrucaria*, *Aureobasidium pullans*, *Candida albicans*, *Candida pseudotropocalis*, *Chaetomium globsum*, *Cladosporium cladosporioides*, *Chlorella vulgaris*, *Dreschslera australiensis*, *Epidermophyton* sp., *Gliomasta cerealis*, *Gloeophyllum trabeum*, *Microsporum* sp., *Microsporum audouinii*, *Monilia grisea*, *Oscillatoria*, *Penicillium chrysogenum*, *Pencillium commune*, *Penicillium funiculosum*, *Penicillium pinophiliumm*, *Penicillium variable*, *Phoma fimeti*, *Pithomyces chartarum*, *Poria placenta*, *Scenedesmus*, *Saccharonyces cerevisiae*, *Scolecobasidium humicola*, *Trichoderma viride*, *Trichophyton interdigitale*, *Trichophyton maidson*, *Trichophyton mentogrophytes*, and *Trichophyton* sp.

Protozoa parasites include, for example, *Cryptosporidium parvum* (oocysts) and *Giardia*.

For more detailed information regarding antimicrobial activity against gram positive bacteria, gram negative bacteria, viruses, fungi, algae, mold, yeast, spores and protozoa parasites, see Hsiao, Y. Chinese Pat. Appl., PCT/CN98/00207 (1998); Malek, J. et at., U.S. Pat. No. 4,259,103 (1981); Klein, S., U.S. Pat. No. 4,394,378 (1983); Eudy, W., U.S. Pat. No. 4,406,892 (1983); Gettings, R. et al., U.S. Pat. No. 4,908,355 (1990) and U.S. Pat. No. 5,013,459 (1991); Blank, L. et al., U.S. Pat. No. 5,145,596 (1992); Avery, R. U.S. Pat. No. 5,411,585 (1995); Blank, L. et al., U.S. Pat. No. 4,865,844 (1989); Battice, D. et al., U.S. Pat. No. 4,631,297 (1986); Higgs, B. et al., U.S. Pat. No. 5,359,104 (1994); Avery, R et al., U.S. Pat. No. 5,411,585 (1995); White, W. et al., *Book of Papers*, 12th Annual Nonwovens Tech. Symposium, pp. 13-46 (1984); McGee, J. et al, *Am. Dyestuff Rep.* 6: 56-59 (1983); Dow Corning Technical Brochure; 22-994-83 (1983); Gettings, R. et al., *Book of Papers, American Association of Textile Chemists and Colorists National Technical Conference*, pp. 259-261 (1978); Dow Corning Technical Brochure, 24-095-85 (1985); Tsao, I. et al., *Biotechnol. Bioeng.*, 34: 639-46 (1989); Tsao, I et al., *ACS Symp. Ser.* 419: 250-67 (1990); Klein, M. et al, *Principles of Viral Inactivation*, $3^{rd}$ Ed., S. Block, Ed., (Lea & Febiger, Philadelphia, Pa.) pp. 422-434 (1983); Peterson, W. et al, U.S. Pat. No. 6,613,755; each of which is incorporated entirely by reference herein.

Conventional quaternary ammonium organosilanes are available as 42% active material in methanol under the trademark DOW CORNING® 5700 (3-(trimethoxysilyl)propyldimethyloctadecyl ammonium chloride) by Aegis Environmental Management, Inc. of Midland, Mich. and Requat 1977 (3-(trimethoxysilyl)-propyldidecylmethyl ammonium chloride) by Sanitized Inc. of New Preston, Conn. Octadecyldimethyl(3-trimethoxysilylpropyl)ammonium chloride (Cat. No. SI06620.0) as a 60% active solution in methanol, tetradecyldimethyl(3-trimethoxysilylpropyl)ammonium chloride (Cat. No. SIT7090.0) as a 50% solution in methanol and didecylmethyl(3-trimethoxysilylpropyl)ammonium chloride (Cat. No. SID3392.0) as a 42% solution in methanol are offered by Gelest, Inc. of Tullytown, Pa. They are often applied from solvent solutions such as lower alcohols.

EXAMPLES

The following examples are provided by way of illustration only and not by way of limitation. Those of skill in the art will readily recognize a variety of non-critical parameters that can be changed or modified to yield similar results.

ODTA: Octadecyldimethyl(3-trimethoxysilyl)propyl ammonium chloride. Obtained from Wright Chemical Corp., Wilmington, N.C. as a 42% active material in methanol. This material may also be named as 3-(trimethoxysilyl)propyl-dimethyloctadecyl ammonium chloride. Also available as a 42% active material from Aegis Environmental Management, Inc., Midland, Mich. marketed as DOW CORNING® 5700.

REQUAT: 3-(trimethoxysilyl)propyldidecylmethyl ammonium chloride. Obtained from Sanitized Inc., New Preston, Conn.; Requat 1977 as a 42% active material in methanol.

TDTA: 3-(trimethoxysilyl)propyltetradecyldimethyl ammonium chloride obtained from Gelest, Inc., Tullytown, Pa., Cat. No. SIT7090.0 as a 50% solution in methanol.

Example 1

A solution suitable for application was prepared by adding 4 parts ODTA to 100 parts deionized water with stirring. The resulting clear solution was applied to an open, polyvinyl chloride (PVC) flat-type evaporation pan by atomized spray, insuring that all surfaces were thoroughly wetted. The pan is allowed to air dry for 24 hours to cure the quaternary ammonium organosilane reagents to the container surface to form a quaternary ammonium organosilane coating. Water containing bacteria level previously measured at $10^7$ total bacteria/ml using a BIOSPERSE® Test Kit was added to the pan in a ratio of 4.6 grams of water per square inch of surface area. After 30 minutes the water is sampled using a BIOSPERSE® test kit. After incubation, $10^5$ bacteria/ml was measured. Resampling of the test water at 1 hour and 4 hours gave bacterial counts of $10^4$ and $<10^3$, respectively.

Example 2

A 4 oz. solution prepared according to Example 1 was added to a 1 pint tin-plated metal test container having 3/4 inch screw top. The solution was agitated to completely wet the inside surface of the container for 1 minute and then decanted. The test container was allowed to air dry for one hour. Residual vapors were removed by an air purge for 5 minutes and the container was then heated to 105° C. for one hour to cure the quaternary ammonium organosilane reagents to the container surface to form a quaternary ammonium organosilane coating. Water (300 g) having a high bacterial count of $10^7$ bacteria/ml was added to the test container. The test container was allowed to stand one hour at room temperature. After two hours, the test water bacterial level was measured at $10^3$ bacteria/ml using a BIOSPERSE® test kit.

Example 3

Two ounce containers of glass, high density polyethylene (HDPE), polypropylene (PP) or polyvinyl chloride (PVC) were treated with an aqueous solution containing 1.5% TDTA. The containers were heated to 100 C for one hour to cure the quaternary ammonium organosilane reagent to the container surfaces to form a quaternary ammonium organosilane coating. Each container was then rinsed with one oz. of deionized water. One ounce of water containing $10^5$ bacteria/ml was added to each container and capped. After 24 hours at room temperature, each container was sampled and bacteria measured with a BIOSPERSE® test kit. All containers indicated bacteria counts of $10^3$ bacteria/ml following incubation for 24 hours.

Example 4

Coiled aluminum test tubing 8 ft. in length and having an internal diameter of 1/4 inch was treated with a solution of 8 parts REQUAT to 100 parts isopropanol. The tube was filled with the solution, sealed and allowed to stand for 15 minutes. The tube was drained and air dried with a stream of compressed air passing through the tube at a rate of 100 ml/minute for 24 hours to cure the quaternary ammonium organosilane reagent to the tubing surfaces to form a quaternary ammonium organosilane coating. An aqueous liquid containing $10^7$ units/ml of bacteria and algae was passed through the coiled aluminum tubing. The aqueous liquid was gravity circulated through the tubing at a rate of 5 ml/minute resulting in contamination of $<10^3$ bacteria/ml.

Example 5

An antimicrobial solution suitable for treatment of silicaeous surfaces including sand and zeolites was prepared by adding 67.5 grams REQUAT to a stirred solution containing 3.375 kg deionized water and 3 grams of 3-aminopropyltrimethoxysilane. One kg of the clear solution was sprayed onto 50 pounds of #20 white silica pool filter sand over 5 minutes in a rotary mixer. The wetted material was mixed with agitation for an additional hour and allowed to air dry 24 hrs to cure the quaternary ammonium organosilane reagent to the sand surface to form a quaternary ammonium organosilane coating. The treated sand was employed in a recirculating water system to reduce microbial contamination from $10^7$ bacteria/ml to $<10^3$ bacteria/ml in 30 minutes of operation as measured by a BIOSPERSE® test kit.

Example 6

Zeolites containing approximately 90% clinoptilolite (Ash Meadows Zeolites, LLC) of 20-40 mesh were thoroughly wetted with a solution containing 7 parts ODTA and 93 parts water. The wet zeolites were allowed to air dry 24 hours and then heated 2 hours at 110° C. in a forced air oven to cure the quaternary ammonium organosilane reagent to the zeolite surfaces to form a quaternary ammonium organosilane coating. The treated zeolites were placed in a 2 inch PVC pipe having an overall length of 38 inches. As described below, dechlorinated water containing known quantities of bacteriophages, bacteria, algae and protozoa were passed through the PVC pipe containing the quaternary ammonium organosilane coated zeolites.

Figure 6:
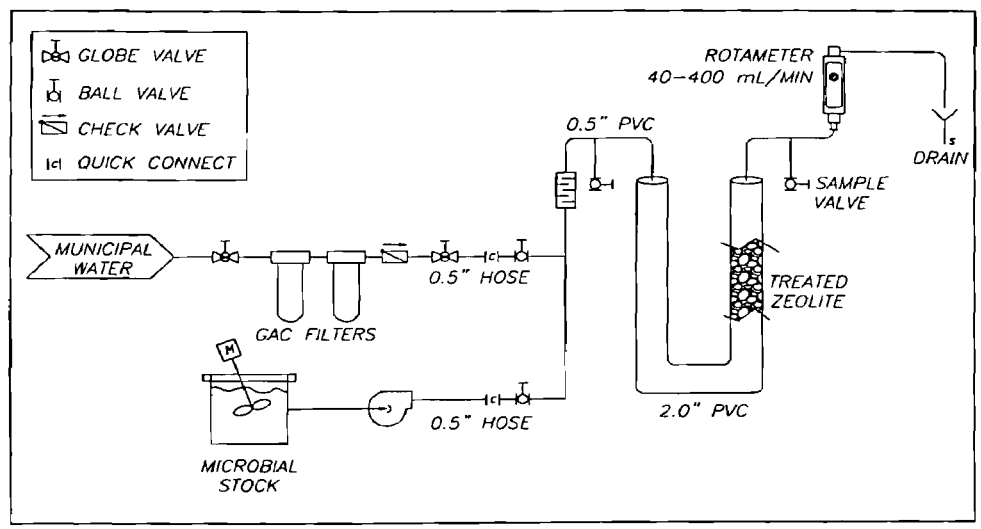

The experimental apparatus consisted of a set of three filters (filter 1, 2 and 3) attached to a manifold, which included fittings for hose connections, and sample ports at the inlet and outlet for each filter (see FIG. 6). An inline mixer was included in the pipe assembly before inlet port to maximize microbial monodispersity. The challenge test water was pumped into each filter at a flow rate of 330 ml/min using a thermally protected pump.

Prior to each microbial challenge, the filters were flushed for 25 minutes with dechlorinated tap water. The flush water was dechlorinated using granular activated carbon filter and chlorine residual was measured before and after the dechlorination using Hach method 8167.

The challenge test water was prepared by adding known number of microorganisms into 20 liters of dechlorinated tap water in a polypropylene container (Nalgene, Rochester, N.Y.). Microbes were washed with 1× phosphate buffered saline just before spiking in the container. The challenge test water container was placed on a stir plate with a Teflon coated stir bar and continuously mixed to provide homogenous distribution of microbes in the influent water. The challenge test water was pumped into each filter using a thermally protected pump (Little Giant Potent Pump, Oklahoma City, Okla.). The pump was primed prior to use by recirculating the microbial stock solution. The hose was connected to the inlet fitting of each filter. The pump was operated for twelve minutes for each filter. The flow rate was measured using a 1000 ml graduated cylinder and adjusted to 330 ml/min as recommended by CSL. Based on the hydraulic parameters of the system, each filter needed a 12-minute-run to stabilize. The effluent samples were taken from each filter after twelve minutes and a single influent sample was collected from the second filter after eight minutes, which represented influent concentration for the complete run. Once the experiment was complete, the filters were again flushed for 30 minutes with dechlorinated tap water.

Example 6.1

Bacteriophages

A series of experiments were conducted with the bacteriophages MS2 and PRD1. The effluent and influent samples were taken and diluted as described above. The samples for MS2 and PRD1 were serially diluted and assayed using their respective bacterial hosts by double layer agar method (Adams, M. H., *Bacteriophages*, Interscience, New York (1959)). The plates were incubated at 37 C for 24 hours, at which time clear virus plaques were counted. The results are presented in FIG. 1. The log removal and inactivation for MS2 and PRD1 ranged between 2.40 to 2.96, and 1.50 to 2.27 log, respectively. The over average removal for MS2 and PRD1 were 2.8 and 2.0 log, respectively. The data shows that quaternary ammonium organosilane coated zeolite can reduce the viable number of bacteriophages in aqueous liquid.

Example 6.2

Bacteria

Figure 2:
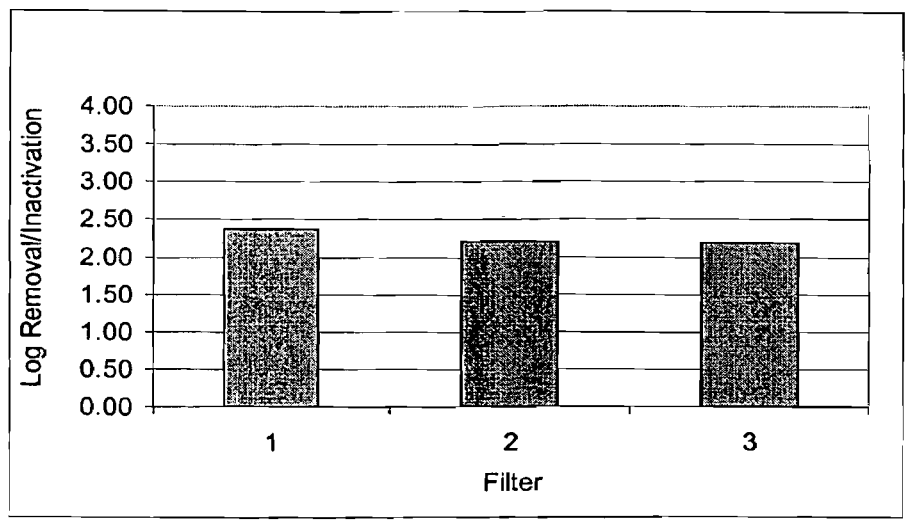
Figure 2:
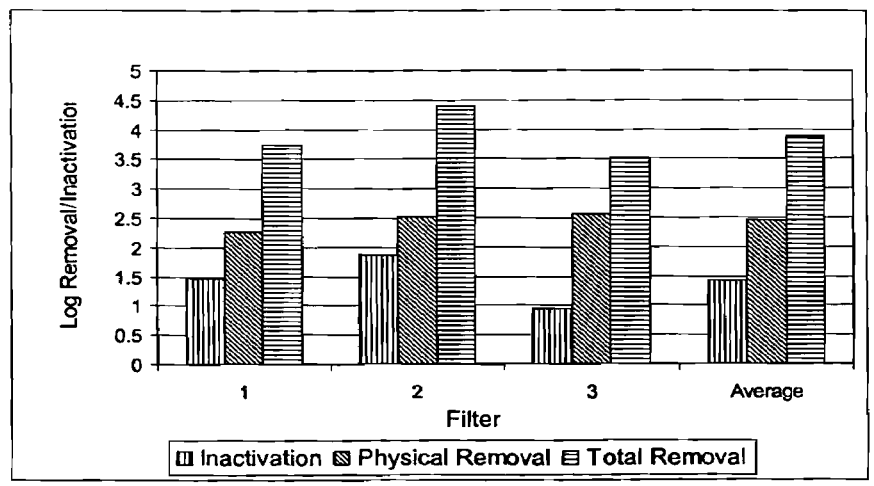
Figure 3:
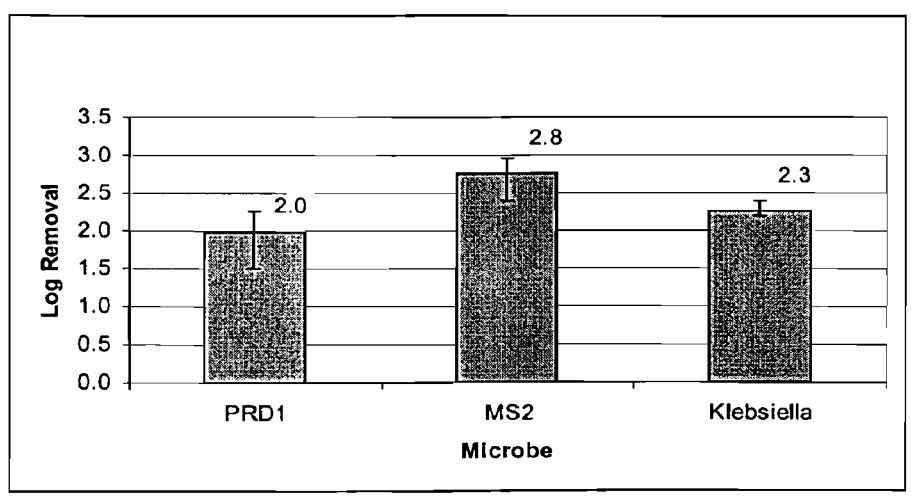

An independent series of experiments were conducted with the bacteria *Klebsiella terriena* and *E. Coli* (ATCC 25922). The effluent and influent samples were taken and diluted as described above. The samples were assayed by membrane filtration techniques using 0.4 µm pore size membrane filter. The membrane filter was placed on a selective medium and incubated at 37 C for 24 hours, at which time bacterial colonies were counted. The results are presented in FIG. 2(A) and (B). As shown in FIG. 2(A) and FIG. 3, consistent removal for *Klebsiella* was observed in all the filters, which ranged from 99.37% (2.2 log) to 99.60% (2.4 log) with an average of 99.50% (2.3 log). As shown in FIG. 2(B), the removal for *E. coli* ranged from 99.96% (3.50 log) to 99.99% (4.39 log) with an average of 99.98% (3.88 log). This study shows that quaternary ammonium organosilane coated zeolite can effectively reduce the viable number bacteria in aqueous liquid.

Example 6.3

Algae

Figure 4:
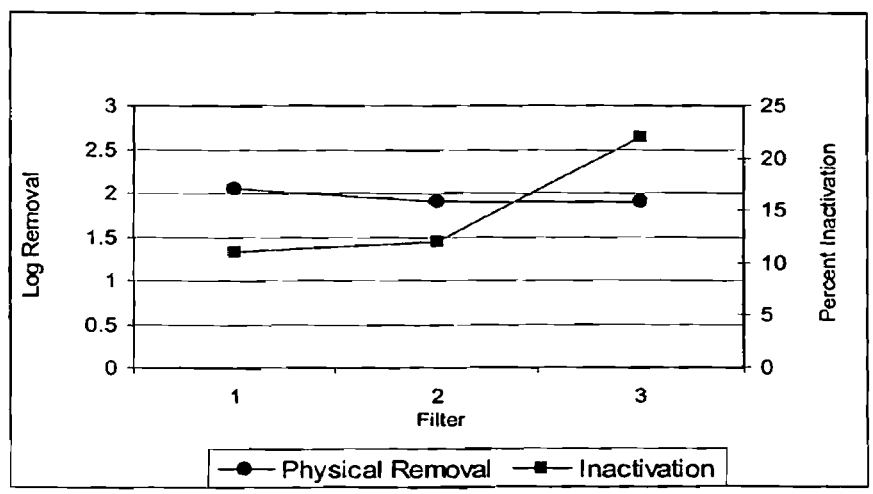

Experiments were conducted with *Chorella vulgaris* to determine both the removal as well as inactivation effects of the media against algae. The effluent and influent samples were taken and diluted as described above. The samples were concentrated by centrifugation before assaying for total removal and inactivation. Removal was determined by total volumetric counts under microscope. The inactivation rate was determined by viability test. The algal cells were digested with 2% trypsin (in hanks balanced salt solution) and stained with Fluorescein Diacetate (Sigma Chemicals F-7378). Fluorescein Diacetate (FDA) is a non-polar ester that passes through cell membranes. Once inside the cell, FDA is hydrolyzed by esterases (an enzyme present in viable cells) to produce fluorescein, which accumulates inside viable cell walls and fluoresce under UV light. A microscope equipped with both white and ultraviolet light, was used to quantify live and dead algal cells. The results are presented in FIG. 4. The average removal of 99.11% (2.05 log), 98.74% (1.90 log) and 98.74% (1.90 log) were observed for filter 1, 2, and 3, respectively. The average of three inactivation measurements for filter 1, 2, and 3 were 11% (0.05%), 12% (0.06 log) and 22% (0.11 log), respectively. However, based on individual measurements the overall range of inactivation for the three filters was 5% (0.02 log) to 46% (0.27 log) and averaged at 15% (0.07 log). It is clear that quaternary ammonium organosilane coated zeolite can effectively reduce the viable number of algae in aqueous liquid.

Example 6.4

Protozoa Parasites

Figure 5:
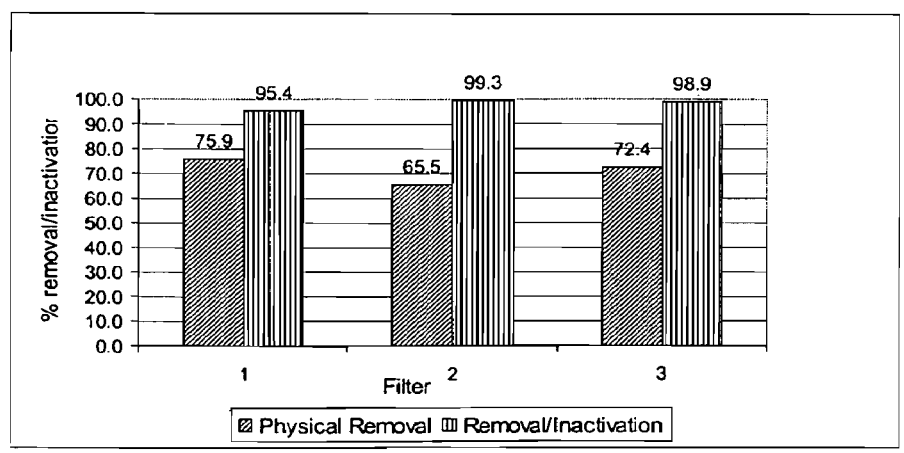

*Cryptosporidium parvum* oocysts were obtained from the Sterling Parasitology Laboratory at the University of Arizona, Tucson, Ariz., and were used to determine the efficacy of removal or inactivation of infectious oocysts. The removal of *Cryptosporidium parvum* oocysts was determined by Hemacytometer counts on concentrated samples, whereas, the number of infectious oocysts were determined by infection foci detection method using cell culture technique with the most-probable-number assay (FDM-MPN) (Slifko et al., *Applied Environmental Microbiology*, 65:3936-3941 (1999)). The results are presented in FIG. 5.

The cumulative removal/inactivation of infectious *C. parvum* oocysts averaged at 97.9% (1.68 log) for all three filters. The removal and inactivation performance by each filter were 95.4% (1.34 log), 99.3% (2.15 log), and 98.9% (1.96 log) for filters 1, 2, and 3, respectively. The removal (only) of oocysts averaged at 71.3% (0.54 log) with an individual removal of 75.9% (0.62 log), 65.5% (0.46 log), and 72.4% (0.56) for filters 1, 2, and 3, respectively. The study indicates that quaternary ammonium organosilane coated zeolite can effectively reduce the viable number pf protozoa parasites in aqueous liquid.

Open Cell Substrates

Various implementations of static fluid disinfecting systems my utilize open-cell (reticulated) foams (both synthetic and natural). In particular implementations, by non-limiting example, the open-cell foam (foam) is composed of one or more cells with structures of, by non-limiting example, tetrakaihedral, fullerene ("bucky-ball"), dodecahedron, tetrakaidecahedron, Weaire-Phelan structures, honeycomb, bitruncated cubic honeycomb (Kelvin structure), octahedral, any combination of the foregoing, and any other polyhedral shape. Implementations utilizing Weaire-Phelan structures may incorporate any of the structures disclosed in D. Weaire et al., "A Counter-Example to Kelvin's Conjecture on Minimal Surfaces," *Phil. Mag. Let.* 69:107-110 (1994), the disclosure of which is incorporated herein entirely by reference. The open-cell foams form an interconnected network of solid struts. In particular implementations, the foam cells are arranged like soap suds, forming a three dimensional, packed array of similarly sized bubble-like structures. These structures may have theoretically maximum volume and minimal surface area for a given volume. When filled with liquid, the resulting structure is similar to an interpenetrating network of polymers.

Foams containing any of the above structures are available in a variety of pore structures as measured in pores per inch (PPI). In various implementations, the pore size in PPI may range from about 10 to about 110. In particular implementations, the pore size may be about 20 to about 40 PPI. In other implementations, the pore size may be 30 PPI and lower. It has been observed that, as the pore size decreases above 110 PPI that the speed and effectiveness of the disinfection decreases. In various open-cell foam materials such as natural open cell foam materials such as sponges, the actual cell size may vary significantly throughout the material (they may have an average PPI within this ranges above), but will also perform in this application following treatment with organosilane quaternary compounds. In various implementations, the open-cell foams are compressible structures and will conform to the shape of the container when suitably sized. In particular implementations, the foam will displace less than about 5% of the liquid volume enclosed in a container when the foam is dimensioned to fill substantially the entire volume of the container. After treatment with organosilane quaternary compounds, the treated foam may be compressed to less than about 25% of their original volume without observable loss of antimicrobial activity.

Foams utilized in implementations of static fluid disinfecting systems disclosed herein may be made of materials including plastics, polymeric materials, stainless steel, copper, silicon, carbon and silicon carbide. In particular implementation, the plastic foams may be composed of virgin or recycled polyethylene terephthalate (PET), polymethylmethacrylate (PMMA). In various implementations carbon foams may compose at least a portion of activated carbon. In implementations where the foam is made of a metallic, semi-metallic, or composite material, the foam may take the form of a mesh structure. Where the foams are made of polyethylene and other plastic materials, they may be those manufactured by New England Foam Products, LLC of Hartford, Conn. In various implementations where the foam takes the form of a mesh, the mesh treated with organosilane quaternary compounds could also be arranged in a three dimensional shape like a mechanical stirring device.

Implementations of antimicrobial foams like those disclosed herein are prepared by applying an aqueous or alcoholic solution containing about 0.1% to about 5.0% by weight of an organosilane quaternary ammonium halide compound to the foam substrate by immersion, pressure spray, electrostatic spray methods, and other methods disclosed in this document. The wetted foams are allowed to air dry or are heated to approximately 120 C to complete curing of the antimicrobial film to the surfaces of the foam cells. When dried/cured, the surface of the foam cell structures contains a substantially uniform film of the organosilane material bonded to the surface through silsesquioxane-like structures. The resultant bonded film is insoluble in water and common solvents and is not removed or leached off during operation in aqueous environments. The coverage of the bonded film on the structure of the foam can be evaluated visually by performing a blue dye test using bromophenol blue. The test is carried out by applying a quantity of bromophenol blue solution to the foam, and after allowing the solution to rest on the foam for about 30 seconds, washing the bromophenol blue solution out of the foam. The portions of the structure of the foam that retain the blue color are those that contain bonded film, as the bromophenol blue couples to the organosilane material and not to the foam material.

In various implementations, the organosilane quaternary compound used for treating may be octadecyldimethyl-(3-trihydroxsilylylpropyl)ammonium chloride. In other implementations, organosilane starting materials for formation of films may include one, all, or any of the following:

Octadecyldimethyl-(3-methoxysilyslpropyl)ammonium chloride: $C_{18}H_{35}(CH_3)_2N^+(CH_3O)_3SiC_3H_7$ $Cl^-$ Tetradecyldimethyl-(3-trimethoxysilylpropyl)ammonium chloride: $C_{14}H_{29}(CH_3)_2N^+(CH_3O)_3SiC_3H_7$ $Cl^-$ Didecylmethyl-(3-trimethoxysilylpropyl)ammonium chloride $(C_{10}H_{21})_2CH_3N^+(CH_3O)_3SiC_3H_7Cl^-$ In various implementations, other substrate reactive organosilanes including ammonium chloride moieties may be utilized. Any of the organosilane compounds disclosed in this document may be employed in various implementations.

In this document, filter media treated with organosilane quaternary ammonium materials are disclosed that remove pathogens from water passing through the filter media of 2 log for bacteria and up to 98% for parasitic protozoa such as *Cryptosporidium parvum*. It was previously theorized that the increased surface area of a media, especially in the case of filter media such as sand or zeolites, would result in increased elimination and inactivation of pathogens dispersed in the water. The foams disclosed herein have a greatly reduced surface area (less than or equal to about 1 $m^2$/gram) when compared with filter media such as filter sand (tens of $m^2$/gram) or zeolites (hundreds of $m^2$/gram), but also demonstrate significant antimicrobial activity when placed in a static container of liquid sufficient to disinfect the fluid. The open-cell foams have a minimal surface area as the foam, during manufacture, seeks to create a maximum volume with a minimum surface area and resulting surface energy (driven by surface tension and surface free energy effects).

It has been observed that organosilane quaternary treated foams manufactured according the principles in this disclosure eliminate and inactivate bacterial, viral and parasitic protozoa pathogens up to 6 log in 10 minutes of static exposure of the pathogen containing liquid to the submerged foam in a container for an effective period of time. Such foams treated with organosilane quaternary compounds have been demonstrated to rapidly and effectively disinfect fluids in which they are in contact by inactivating and eliminating a wide variety of pathogens including viruses (encapsulated and non-encapsulated), algae, gram positive bacteria, gram negative bacteria and parasitic protozoa including *Cryptosporidium parvum* and *Giardia*. Similar to the other antimicrobial compounds disclosed herein, the disinfection process is non-leaching and imparts no detectable antimicrobial agent or compounds into the contacting fluid. An example of the performance of an implementation of a treated foam is found below:

Example 7

Twenty samples of water containing bacteria, viruses, and *Cryptosporidium* oocytes were treated according to the standards in the NSF International P248 test for Military Operations Microbiological Water Purifiers. Passage of the test requires that within a maximum of 20 minutes for all 20 samples, the bacterial population decrease by 6 log, the viral population decrease by 4 log, and the *Cryptosporidium* oocytes be reduced by 3 log. When foams treated with 1-Octadecanaminium, N,N-dimethyl-N-(3-(trimethoxysilyl)propyl)-chloride were placed in the twenty samples, remaining in static contact with the water, in 10 minutes 18 of the 20 samples met the test criteria, and by 15 minutes, all 20 samples had experienced microbe reduction to the desired testing levels. In this case, the effective period of time was reached when residual microorganism levels in all the samples reached the desired reduced level, in 15 minutes.

Unlike the use of treated filter media discussed earlier in this document, the disinfection process occurs under static conditions of little to no fluid flow over the treated surface of the foam and is accordingly not a filtration process for pathogen removal. Because the foams are suitable for use in non-flowing, fluid conditions they may be useful for antimicrobial stabilization of fluids for extended periods in containers. Fluids in contact with treated foams may be stored for extended periods without microbial growth or the need for external influences such as refrigeration. Because of this, implementations of treated foams like those disclosed herein may be incorporated in fluid transport vehicles, such as milk tanker trailers, and other bulk foodstuff transport vehicles and systems. An additional benefit for vehicles like milk tanker trailers is that if the foams are attached at regular intervals along the internal circumference of the tank with a dimension extending radially into the milk payload, they will have a baffling effect, reducing momentum flow effects of the milk moving around during transport. However, because the foams are antimicrobial, the problems of trying to clean a conventional tank with metal baffles may be eliminated. In some implementations, gravity fed flow filtration using treated foams may be used, provided it is carried out at low pressures that do not mechanically harm the films.

This result of increased efficacy of the open-cell treated substrate when compared with the performance of organosilane treated filter media is unexpected. This is because the surface area of foam media contacting the contaminated fluid is far less than filter media. For example, the surface area per volume of the foam implementations when compared with the surface of zeolite and sand is millions of times smaller. For example, the surface area of a zeolite ranges in the hundreds of square meters per gram. In contrast, a treated foam with a surface area of just 36.4 square feet can disinfect a water bladder that holds 2.5 liters of water. This disinfection using foams takes place rapidly (90 seconds-15 minutes) compared to previous systems that involved coating the interior surface of a bottle with organosilane materials (3 hours). Being able to obtain orders of magnitude improved inactivation or similar inactivation of microbes as with use of treated filter media from a foam with orders of magnitude less surface area employed in a non-forced flow, static fluid operating condition is an unexpected result which runs contrary to conventional knowledge of those of ordinary skill in the art.

Once prepared by coating with organosilane quaternary ammonium compounds, the treated foams can be stored outside liquid for greater than 5 years and still retain their antimicrobial activity. Because of this, the effective antimicrobial lifetime of a treated foam is determined by the ability of the particular underlying foam material to withstand prolonged exposure to the fluid without beginning to shed or otherwise breakdown mechanically within the fluid. This means that the limit to the volume of liquid that could be potentially treated by a coated foam is the mechanical lifetime/stability of the foam.

Implementations of foams like those disclosed herein are capable of disinfection of clear and turbid water as well as visually opaque fluids including food juices, plant extracts, milk, and milk products. These foams may be particularly useful for visually opaque fluids as conventional methods of fluid disinfection include widespread use of energy intensive ultraviolet (UV) radiation for which the fluid must be transparent. Because the foams do not require adding any liquid matter to the liquid or leach into the fluid, they contrast with other conventional methods which require the addition of toxic, fluid soluble compounds including energy intensive and toxic ozone or equally toxic, carcinogen-producing chlorine, iodine, chlorine dioxide and chloramines. Implementations of foams like these disclosed may be used to disinfect cutting or fracking fluids (hydrocarbon [oil] and water mixtures) as well as any other flowable liquid that does not contain particulates that would clog the foam. Implementations of foams like those disclosed herein may also be employed to disinfect solid materials, such as powders that are dispersable and can contact the foam. In other implementations, implementations of the foams may be used to provide disinfection of solids and liquids through surface contact. For example, in meat packaging, the meat may be laid down on a piece of treated foam (which may be the packaging container in particular implementations), which will act to kill microbes in the meat and in liquids associated with the meat during transport and storage prior to food preparation. In such implementations, one or more surface of the meat (or other solid) are contacted by the foam.

Implementations of static fluid disinfecting systems employing open-cell foams like those disclosed herein may employ various implementations of a method of disinfecting a fluid. Implementations of the method include statically contacting a fluid containing one or more microorganisms with a foam coated with any one of the quaternary organosilanes disclosed herein in a container that encloses the foam and holds the fluid. The fluid may contain one or more of any of the microorganisms disclosed herein. In various implementations of the method, the method may include statically contacting one or more surfaces of a solid included in the container with the foam. This solid could be any disclosed in this document, including foodstuffs and other solid materials that contain one or more microorganisms.

In places where the description above refers to particular implementations of static and flowing fluid disinfecting systems and implementing components, sub-components, methods and sub-methods, it should be readily apparent that a number of modifications may be made without departing from the spirit thereof and that these implementations, implementing components, sub-components, methods and sub-methods may be applied to other static and flowing fluid disinfecting systems. For example, the features of the reagents of the present invention are equally applicable to the coatings of the present invention described herein.

What is claimed is:

1. A method of disinfecting a fluid, the method comprising:
    statically contacting a fluid comprised in a container with an open-celled foam, the open-celled foam coated with a quaternary organosilane coating produced from a quaternary ammonium organosilane reagent having the formula:

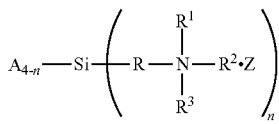

wherein A is a member independently selected from the group consisting of —OR$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; and wherein R$^4$ is a member selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; and R is substituted or unsubstituted alkylene;

R$^1$, R$^2$, and R$^3$ are members each independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl; and substituted or unsubstituted heteroaryl;

Z is a member selected from the group consisting of fluoride, chloride, bromide, iodide, tosylate, hydroxide, sulfate, and phosphate; and n is 1, 2, or 3; and wherein the fluid comprises one or more microorganisms; and achieving a 6 log reduction of bacteria, a 4 log reduction of viruses, and a 3 log reduction of *Cryptosporidium* oocytes after statically contacting with the foam for 15 minutes.

2. The method of claim 1, wherein statically contacting the fluid comprised in the container with the open-celled foam further comprises wherein the open-celled foam comprises a range of pores per inch (PPI) between 10 PPI and 110 PPI.

3. The method of claim 1, wherein statically contacting the fluid comprised in the container further comprises wherein the one or more microorganisms in the fluid are selected from the group consisting of *Cryptosporidium parvum, Giardia*, encapsulated viruses, and non-encapsulated viruses.

4. The method of claim 1, further comprising statically contacting one or more surfaces of a solid material comprising one or more microorganisms comprised in the container with the open-celled foam.

* * * * *